United States Patent
Wegner et al.

(10) Patent No.: US 9,921,153 B2
(45) Date of Patent: Mar. 20, 2018

(54) METHOD FOR SEGMENTING THE DATA OF A 3D SENSOR PRODUCED IN THE PRESENCE OF AEROSOL CLOUDS FOR INCREASING THE SITUATIONAL AWARENESS AND THE LOCATION DETECTION OF OBSTACLES

(71) Applicant: AIRBUS DS ELECTRONICS AND BORDER SECURITY GMBH, Taufkirchen (DE)

(72) Inventors: Matthias Wegner, Friedrichshafen (DE); Thomas Muensterer, Tettnang (DE)

(73) Assignee: AIRBUS DS ELECTRONICS AND BORDER SECURITY GMBH, Taufkirchen (DE)

( * ) Notice: Subject to any disclaimer, the term of this patent is extended or adjusted under 35 U.S.C. 154(b) by 0 days.

(21) Appl. No.: 15/208,907

(22) Filed: Jul. 13, 2016

(65) Prior Publication Data
US 2017/0023473 A1    Jan. 26, 2017

(30) Foreign Application Priority Data
Jul. 21, 2015   (EP) .................................... 15002153

(51) Int. Cl.
*G01B 11/00*   (2006.01)
*G01N 21/53*   (2006.01)
(Continued)

(52) U.S. Cl.
CPC ............. *G01N 21/53* (2013.01); *B64C 27/04* (2013.01); *B64D 45/08* (2013.01); *G01S 7/4876* (2013.01);
(Continued)

(58) Field of Classification Search
CPC ...... G01S 13/913; G01S 13/94; G01S 13/867; G01S 13/86; G01S 13/89; G01N 21/53; B64D 45/08; B64C 27/04; G06K 9/00201
(Continued)

(56) References Cited

U.S. PATENT DOCUMENTS 6,650,276 B2 * 11/2003 Lawless .................... G01S 7/35
                                                                    342/159
7,365,652 B2    4/2008 Scherbarth
(Continued)

FOREIGN PATENT DOCUMENTS

DE       102009035191 A1    2/2011
EP           1650534 A1     4/2006
(Continued)

OTHER PUBLICATIONS

Dietmayer et al., "Model Based Object Classification and Object Tracking in Traffic Scenes from Range Images," Proceedings of the Intelligent Vehicles Symposium, Jan. 1, 2001.
(Continued)

*Primary Examiner* — Hoa Pham
(74) *Attorney, Agent, or Firm* — Patent Portfolio Builders PLLC

(57) ABSTRACT

A method for segmenting the data of a 3D sensor produced in the presence of aerosol clouds and for increasing the situation awareness and the location detection of obstacles involves transforming the sensor data are transformed into a 3D measurement point cloud, determining related subsets as measurement point clusters from the 3D measurement point cloud of an single measurement cycle of the 3D sensor based on the local measurement point density, determining at least one of the characteristic parameters of the individual measurement point clusters, the characteristic parameters including position, orientation in space, and shape, and determin-
(Continued)

Figure 1:
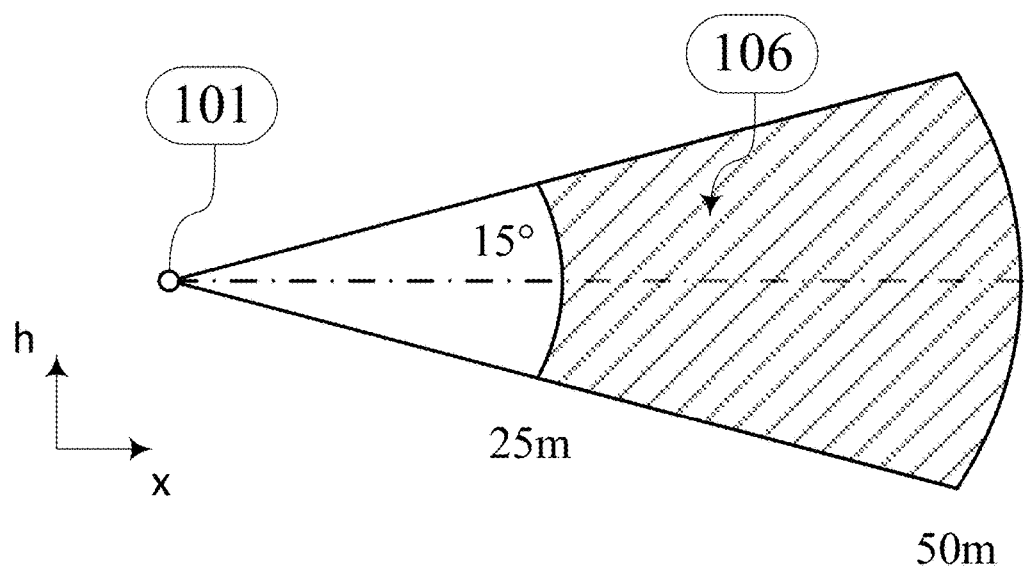

ing a time variation of the characteristic parameters using the recorded parameters calculated from subsequent measurement cycles, from which the association of a measurement point cluster with a real obstacle or with the aerosol cloud results.

18 Claims, 12 Drawing Sheets

(51) Int. Cl.
- *G01S 17/93* (2006.01)
- *G01S 7/487* (2006.01)
- *B64C 27/04* (2006.01)
- *B64D 45/08* (2006.01)
- *G01S 17/89* (2006.01)
- *G06T 7/10* (2017.01)

(52) U.S. Cl.
CPC ........... *G01S 17/89* (2013.01); *G01S 17/933* (2013.01); *G06T 7/10* (2017.01)

(58) Field of Classification Search
USPC ........... 356/335–343, 601–623; 342/33, 159, 342/175, 22, 63
See application file for complete search history.

(56) References Cited

U.S. PATENT DOCUMENTS

| | | | |
|---|---|---|---|
| 8,305,238 B2* | 11/2012 | Wegner | G01C 23/00 340/946 |
| 8,781,790 B2* | 7/2014 | Zhu | G01S 7/4802 342/95 |
| 8,803,727 B2 | 8/2014 | Muensterer et al. | |
| 2007/0076202 A1* | 4/2007 | Cantin | A01M 7/0096 356/338 |
| 2011/0313722 A1 | 12/2011 | Zhu et al. | |
| 2012/0029869 A1 | 2/2012 | Muensterer et al. | |
| 2015/0134251 A1* | 5/2015 | Bixel | G05B 13/04 702/3 |
| 2015/0198735 A1* | 7/2015 | Muensterer | G01S 17/89 702/5 |
| 2016/0195386 A1* | 7/2016 | Yoon | G01S 17/42 356/601 |

FOREIGN PATENT DOCUMENTS

| | | |
|---|---|---|
| EP | 2418510 A1 | 2/2012 |
| EP | 2634597 A1 | 9/2013 |
| EP | 2884305 A1 | 6/2015 |

OTHER PUBLICATIONS

European Search Report dated Jan. 19, 2016 in corresponding EP Application No. 15002153.3.

* cited by examiner

D normalized to [0,1] (cf. Equation (29))

METHOD FOR SEGMENTING THE DATA OF A 3D SENSOR PRODUCED IN THE PRESENCE OF AEROSOL CLOUDS FOR INCREASING THE SITUATIONAL AWARENESS AND THE LOCATION DETECTION OF OBSTACLES

CROSS-REFERENCE TO RELATED APPLICATIONS

This application claims priority 35 USC § 119 to European application 15 002 153.3, filed on Jul. 21, 2015, the entire content of which is herein expressly incorporated by reference.

BACKGROUND AND SUMMARY OF THE INVENTION

Exemplary embodiments of the invention are directed to a method for segmenting data of a 3D sensor produced in the presence of aerosol clouds for increasing the situational awareness and the location detection of obstacles in order to prevent a loss of the spatial orientation in the event of visual impairment due to the aerosol cloud.

In arid, desert-like areas, such as for example Afghanistan, Iraq or Syria, a strong turbulence of sand and dust particles, a form of aerosol cloud, often occurs during remote landings of rotary wing aircraft, such as for example helicopters. The effect is caused by the so-called downwash of the main rotor or the rotors of the aircraft. The chaotic sand and dust turbulences result in complete or partial loss of pilot vision outside the cockpit—the so-called brownout. Other forms of aerosol clouds such as whiteouts (turbulent snow during the landing), smoke, or fog hinder the view and can also significantly restrict the situational awareness of the pilot in a hazardous manner. Due to the absence of a view or the limited external cockpit view there is a risk of the loss of spatial orientation above the ground, in particular with respect of pitch and roll angles as well as unintended lateral drift of the landing aircraft. Moreover, location detection of obstacles in the landing zone is severely limited. All of this increases flying accidents.

Actual sensor data for the landing zone are required to enable a synthetic spatial view and orientation aid for the pilot for maintaining the situational awareness and the location of obstacles. For this purpose, different systems (for example radar, laser, camera systems, GPS etc.) are used.

German patent document DE 102009035191 A1 describes a radar sensor applied to a synthetic display of the surroundings, which in the event of a brownout is supplied with additional data of a radar sensor that is activated for this purpose.

With radar systems, however, significant problems can occur due to so-called crosstalk during the measurement of the landing area that is only a few meters away with simultaneous strongly varying pitch angles during the final landing process as well as due to echoes from side lobes.

Laser sensors have a much higher spatial resolution compared to radar systems due to the short wavelengths thereof, for example 1.5 µm, and are therefore considerably better suited to detecting important details of the situation environment as well as hazardous obstacles (such as for example high voltage lines) in the landing zone of a helicopter. However, laser sensors, as optical systems in contrast to radar systems, can often not fully penetrate a brownout-cloud, because the laser pulses are already reflected back to the sensor, scattered or absorbed by parts of the turbulent dust cloud. In the received laser measurement data, in general parts of the brownout cloud conceal the free view of the landing area lying behind the cloud and any obstacles that may exist.

The physical property of laser sensors makes them appear superficially as less suitable for assisting pilots during brownout landings.

U.S. patent document US 2011/0313722 A1 discloses a method based on laser sensor data with which a correlation of the falling edge of a laser echo with a threshold value takes place, wherein there is a measurement technology difference between obstacles and aerosol clouds.

In known numerical calculation methods, by which turbulent dust of a brownout cloud can be segmented, a global accumulation of all sensor measurement data from multiple numbers of complete (laser) sensor recording cycles (so-called sensor frames) is carried out. During this, very large amounts of data are accumulated. Following the accumulation, it is attempted to determine statistical properties of the measurement points that should enable dust measurement points to be distinguished from real static obstacle measurement points.

The disadvantage of this type of method is that conclusions regarding local properties of individual isolated dust measurement points are based on a very large, global database by means of the accumulation of all measurement points of multiple sensor frames. This may result in very large computation efforts and inefficient processing time.

Exemplary embodiments of the present invention are directed to a method for more efficient and more precise detection of measurement points of an aerosol cloud in real time based on laser sensor data for (significantly) increasing the situational awareness and the location detection of real obstacles.

The method according to the invention for segmenting the data of a 3D sensor produced in the presence of aerosol clouds in order to achieve an increase of the situational awareness and the location detection of obstacles includes the following process steps/processing steps:
1. Transforming the sensor data into a 3D measurement point cloud,
2. Determining connected subsets of the 3D measurement point cloud, so-called measurement point clusters, based on the local measurement point density. This step is performed based on the sensor data of a single measurement cycle of the 3D sensor,
3. Determining at least one of the following characteristic parameters of the individual measurement point clusters determined in step 2:
   position,
   orientation in space,
   shape
4. Determining the variation with time of the characteristic parameters using the sensor data recorded in subsequent measurement cycles, from which the association of a measurement point cluster with a real obstacle or with the aerosol cloud results.

The present method for segmenting sensor data for increasing the situation awareness, in particular of a vehicle driver, and the location detection of obstacles within an aerosol cloud (for example a brownout cloud) is preferably performed in combination with the use of a laser sensor system, wherein such a system can comprise, for example, the following components: a 3D laser sensor for detecting obstacles, an electronic data analyzer for the recorded measurement cycles (so-called sensor frames), and an output device (for example a display screen), wherein the system or parts thereof can be integrated within other systems or can collaborate with other systems by transferring and exchanging or transmitting and receiving suitable data.

The method according to the invention enables reliable detection of real obstacles within the scanned aerosol cloud/turbulence.

The invention can be used for all the situations mentioned in which there is a visual impairment/restriction of the external cockpit view by dust, smoke or fog or turbulence of the elements, including for example known phenomena such as brownouts (dust/sand turbulence) or whiteouts (turbulent snow).

It is irrelevant to this whether the brownout situation is caused by the rotor downwash of a landing rotary wing aircraft or aircraft with vertical takeoff and landing capability or by natural phenomena (i.e. conditions similar to brownout), such as wind or other weather effects or even by the movement of other (airborne) vehicles.

The invention will be described below using a brownout situation representative of all forms of aerosol clouds.

The method according to the invention is based on the numerical analysis of high-resolution 3D data. The 3D data are advantageously recorded in real time before and during the brownout landing by a laser sensor that is typically mounted on the helicopter (such as for example a SferiSense® sensor of the Airbus Defence and Space GmbH, Ottobrunn, Germany), wherein the use is not limited to flying or moving vehicles, but is also possible in static systems.

The methods of the present invention provide reliable detection of turbulent dust or sand of the brownout cloud from the 3D measurement data of a laser sensor, and hence provides for the segmentation of the same from real obstacles, wherein the segmentation is carried out using cluster formation and characteristic parameters of those clusters. The discrimination of the association of a measurement point with the brownout cloud is performed by the analysis of the variation with time of the cluster parameters. Due to the special form of processing for the dust segmentation, the disadvantage of laser sensors during brownout landings is negated and looking through the dust cloud can be practically carried out, which advantageously results in significantly increasing the situational awareness, in particular for a pilot, and the location detection of obstacles.

The calculation method according to the invention and described in detail in the figures reverses the logic of known methods. The basis of those methods is a global accumulation of all sensor measurement data from multiple numbers of complete recording cycles of the sensor field of view (FOV). Due to the reversal of the processing logic of known dust cluster calculation methods and systems from global→local to local→global, a significant efficiency gain results for the processing of the 3D data.

The procedure enables very computationally efficient processing and accurate, practical frame-accurate calculation results to be obtained, whereas the known methods require the accumulation of 3D data over a number of multiple sensor frames for their mathematical analysis. In this respect the present invention represents a completely novel approach to the solution of the problem of aerosol/dust cloud detection and segmentation using laser sensors.

Thus, a real-time capable avionic system for pilot support that is suitable for operational use is provided, which facilitates helicopter landings, especially under brownout/whiteout conditions, and significantly reduces the risk of accidents.

The use of the method according to the invention is not however restricted to aircrafts. A corresponding system can also be advantageously implemented in other vehicles or even at static positions. The use of the information obtained with the method can be carried out by a vehicle driver or a machine, for example an autonomous system.

BRIEF DESCRIPTION OF THE DRAWING FIGURES

The invention is described, inter alia, using specific numerical example calculations based on real measurement data with reference to FIGS. 1 to 15.

Figure 2:
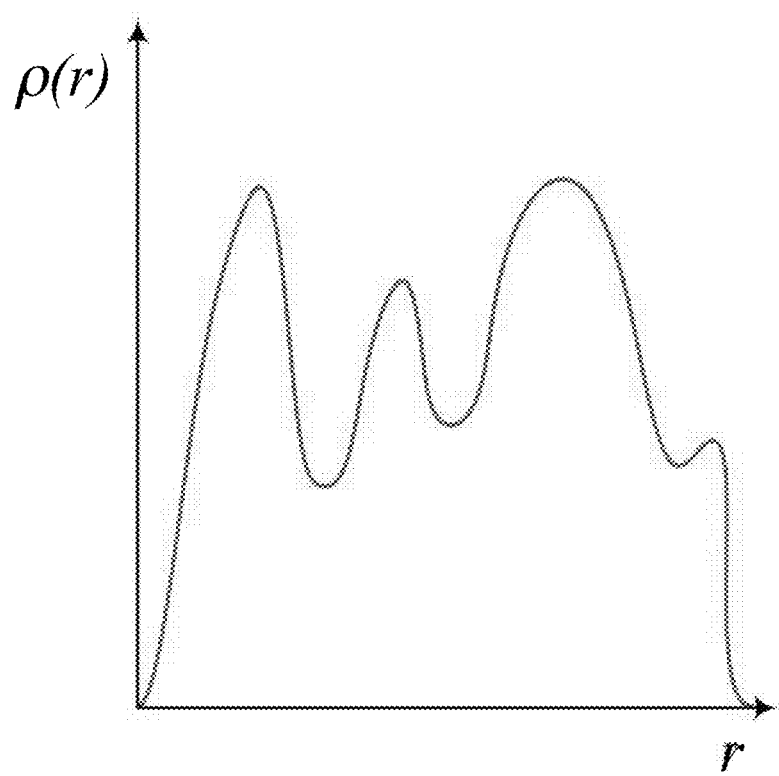
Figure 3:
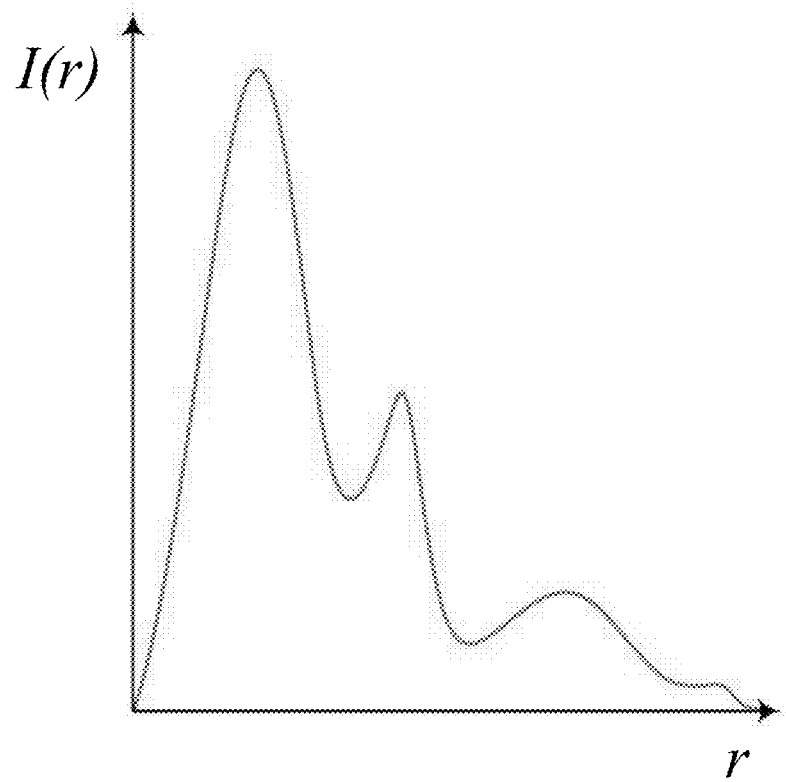
Figure 4:
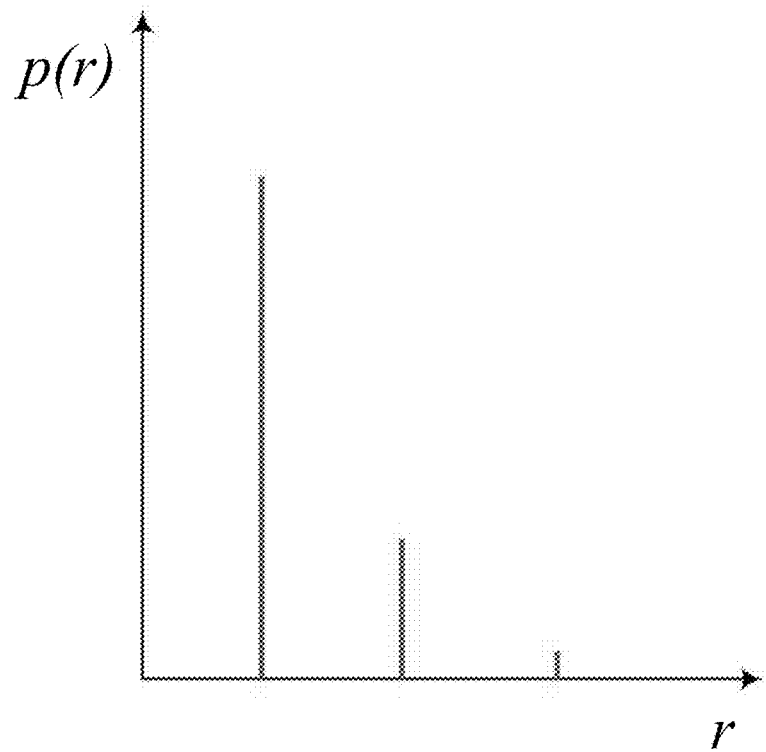
Figure 5:
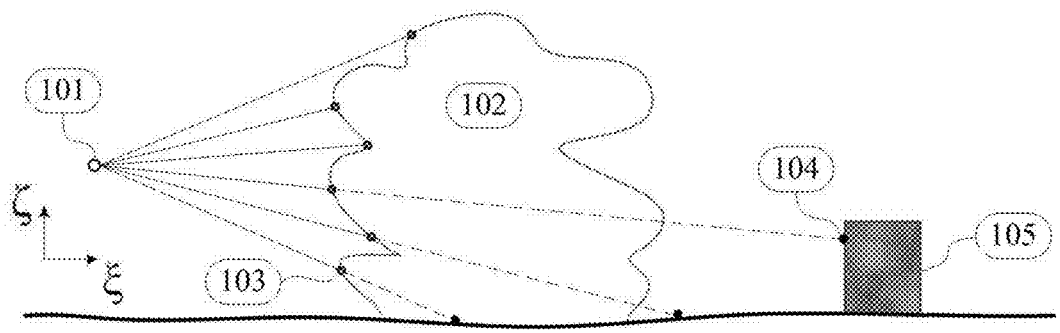
Figure 6:
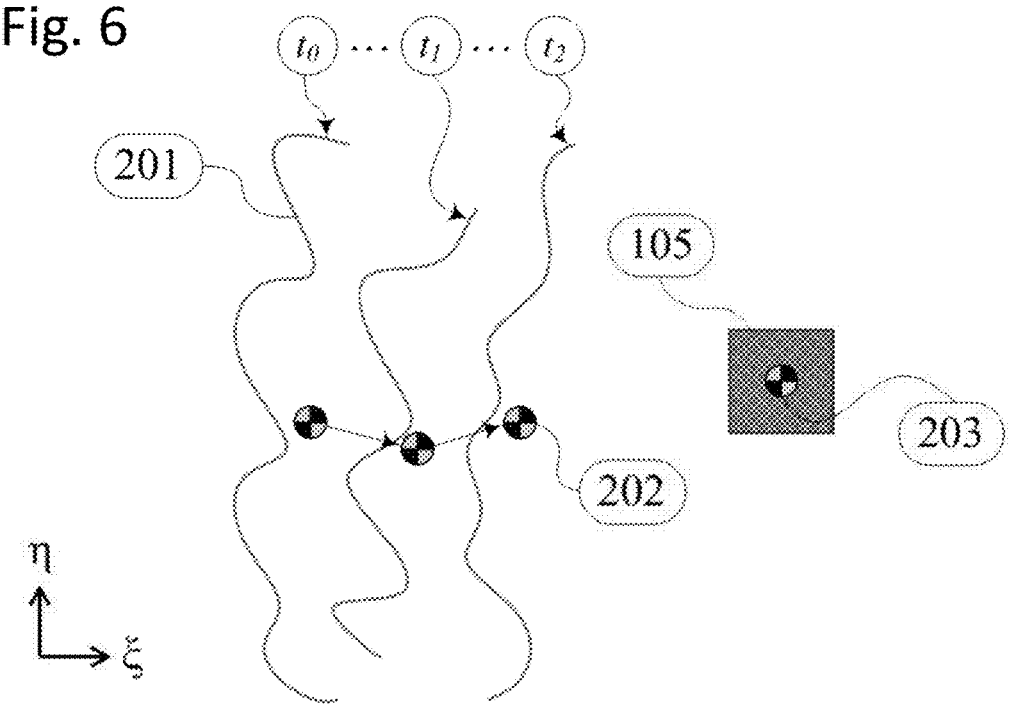
Figure 7:
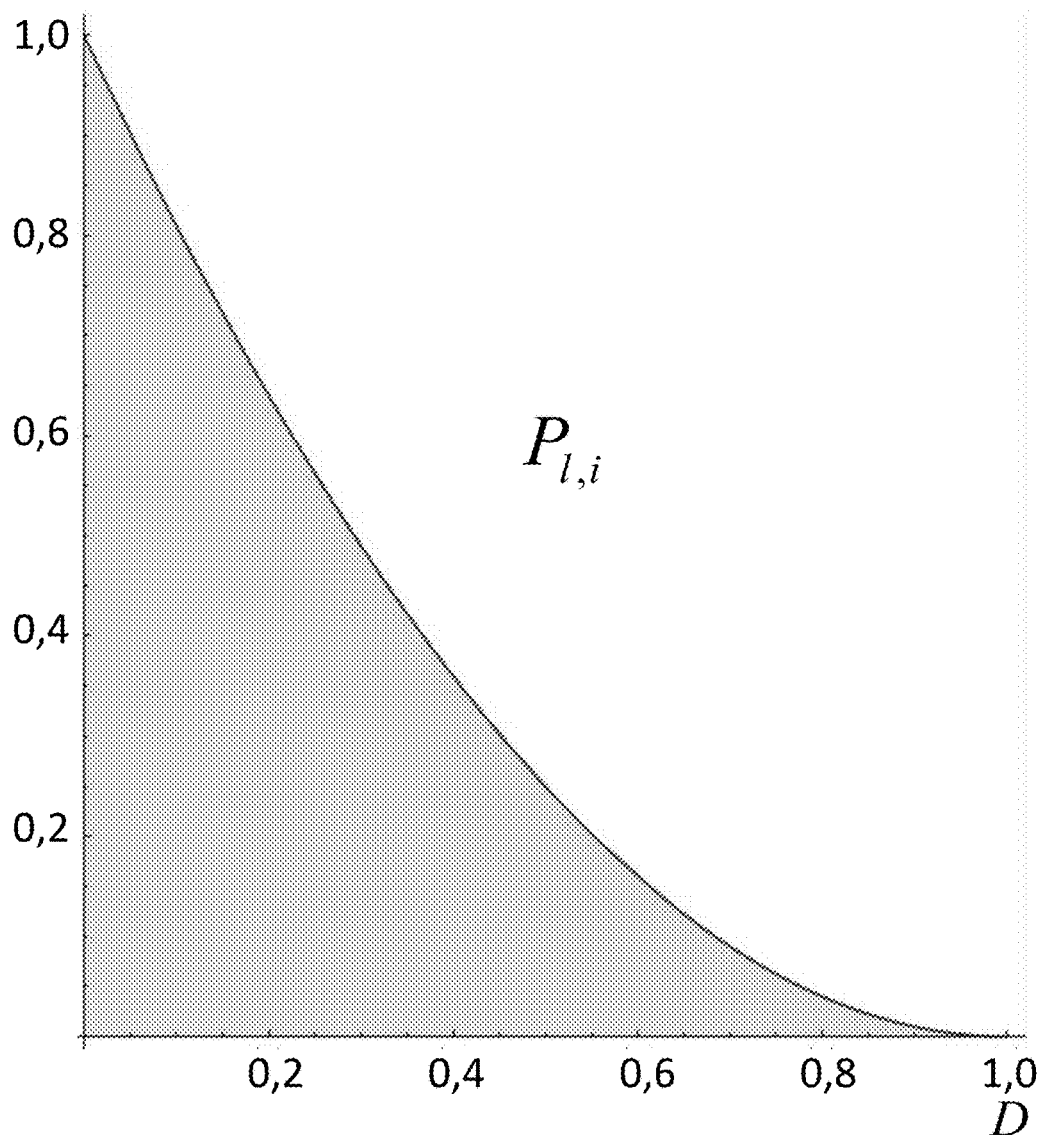
Figure 8:
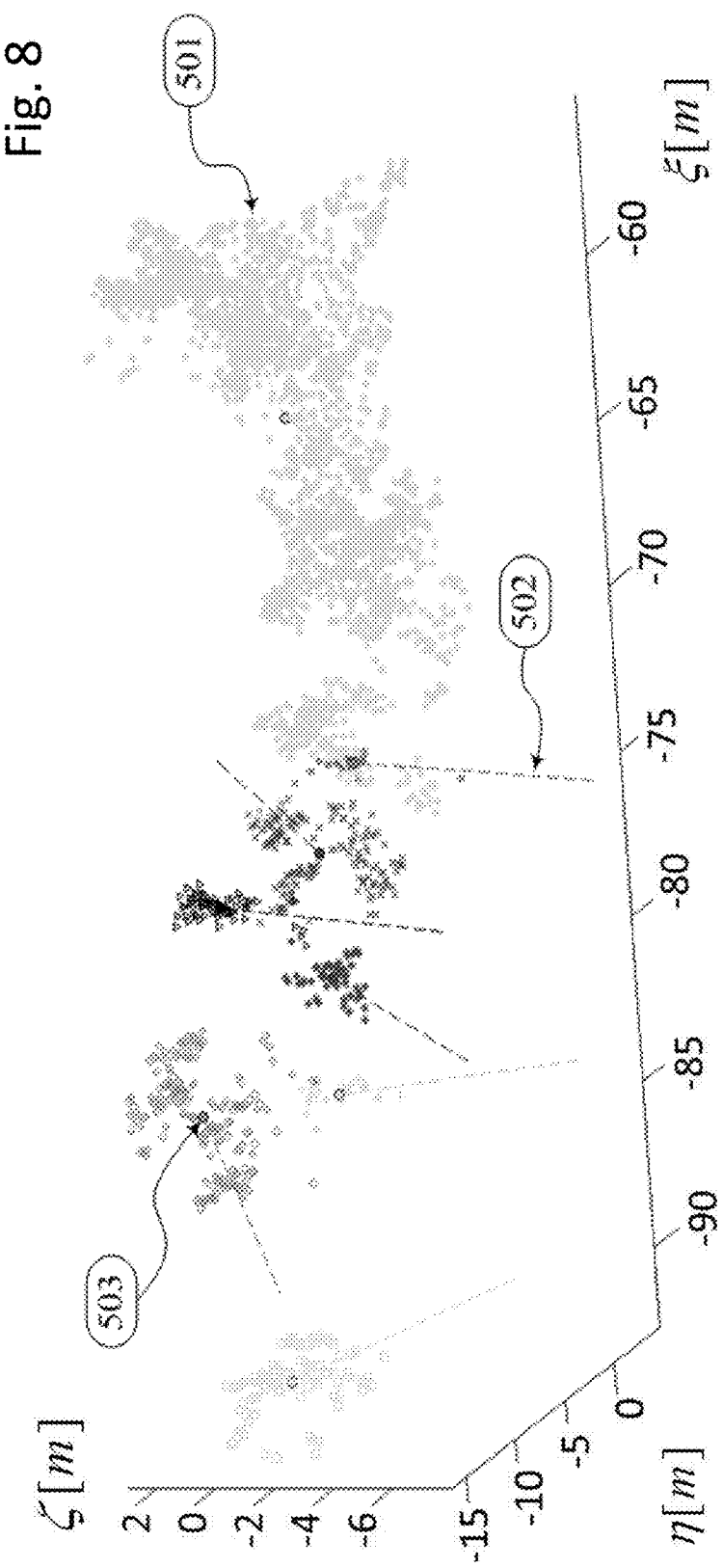
Figure 9:
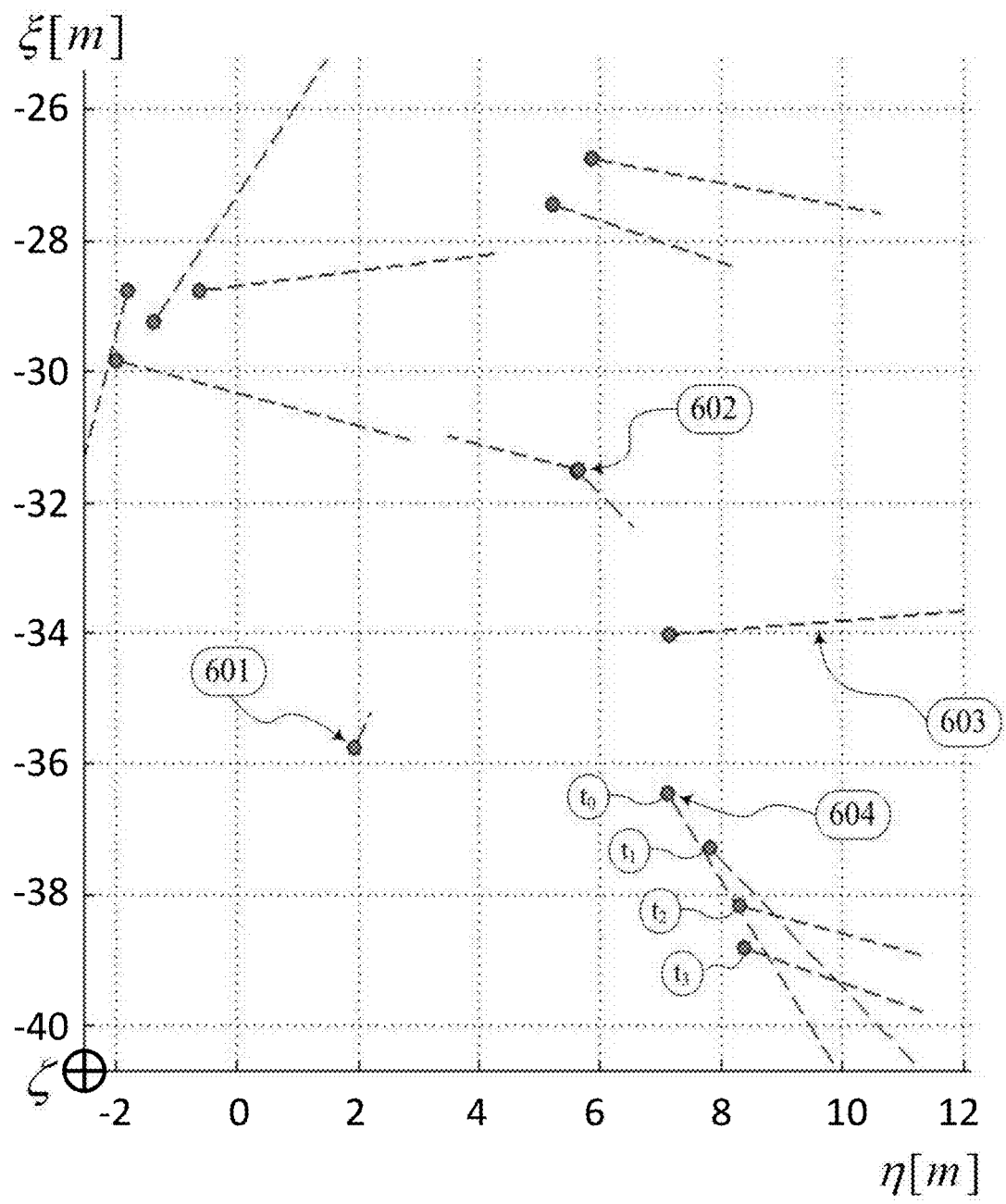
Figure 10:
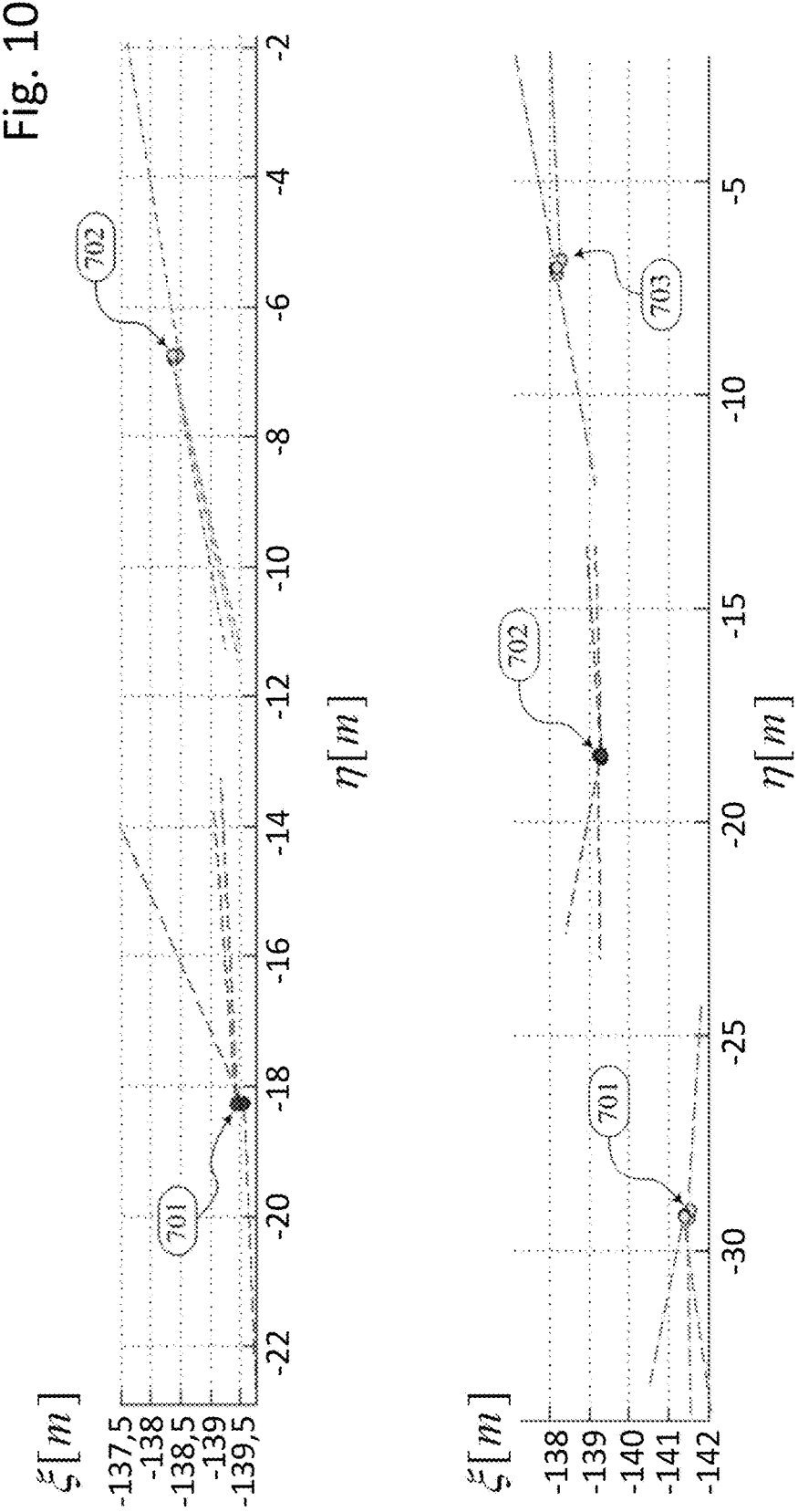
Figure 11:
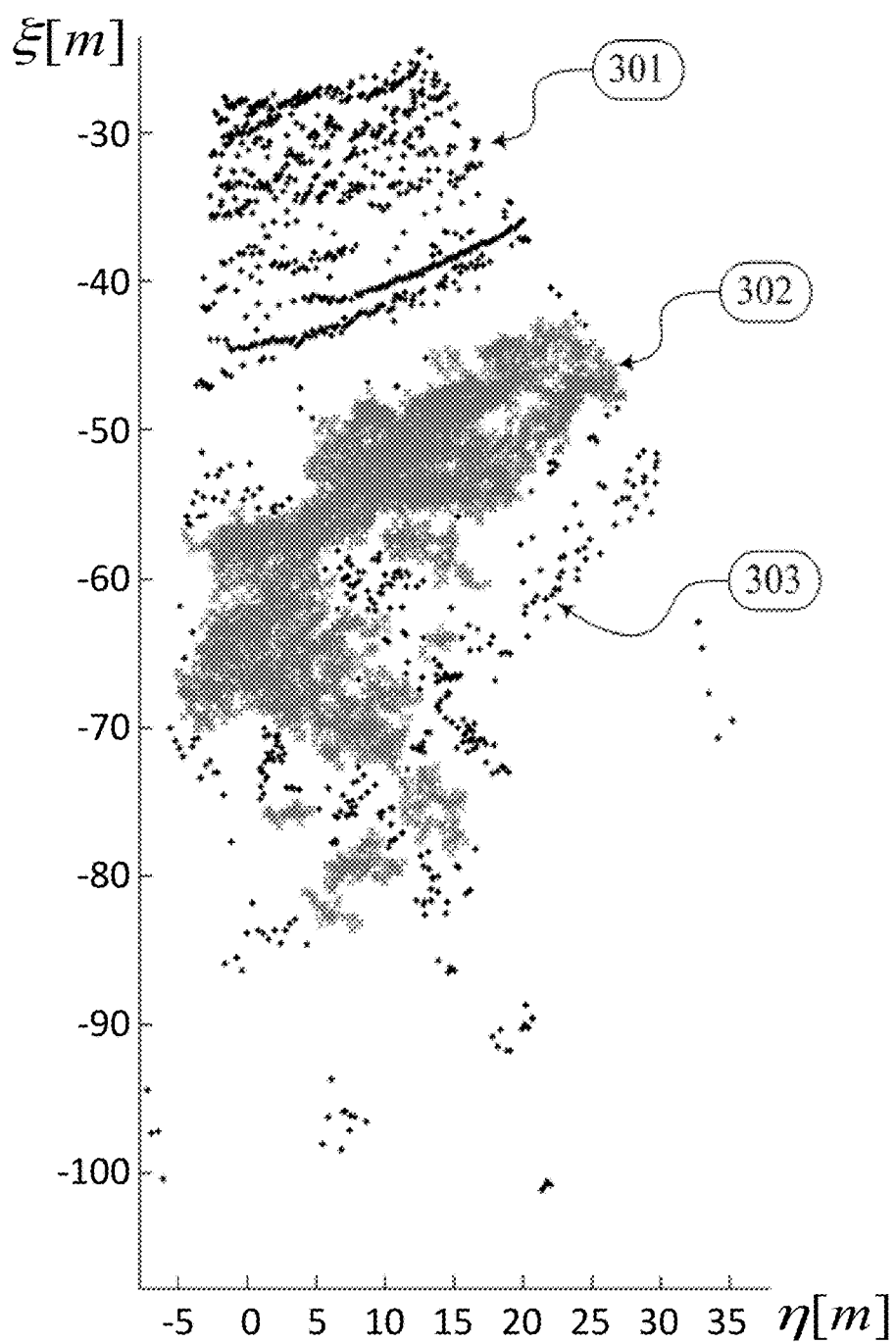
Figure 12:
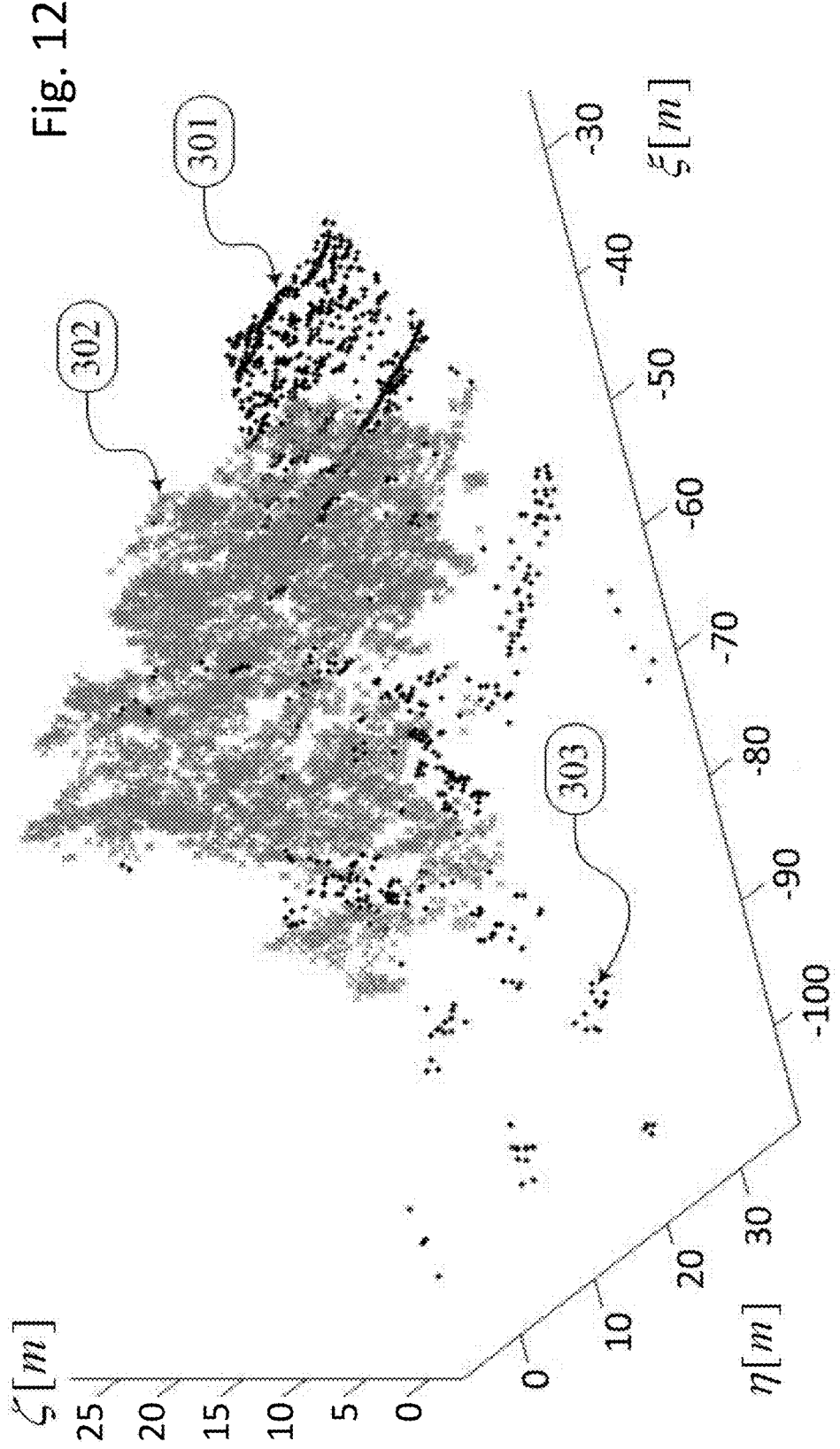
Figure 13:
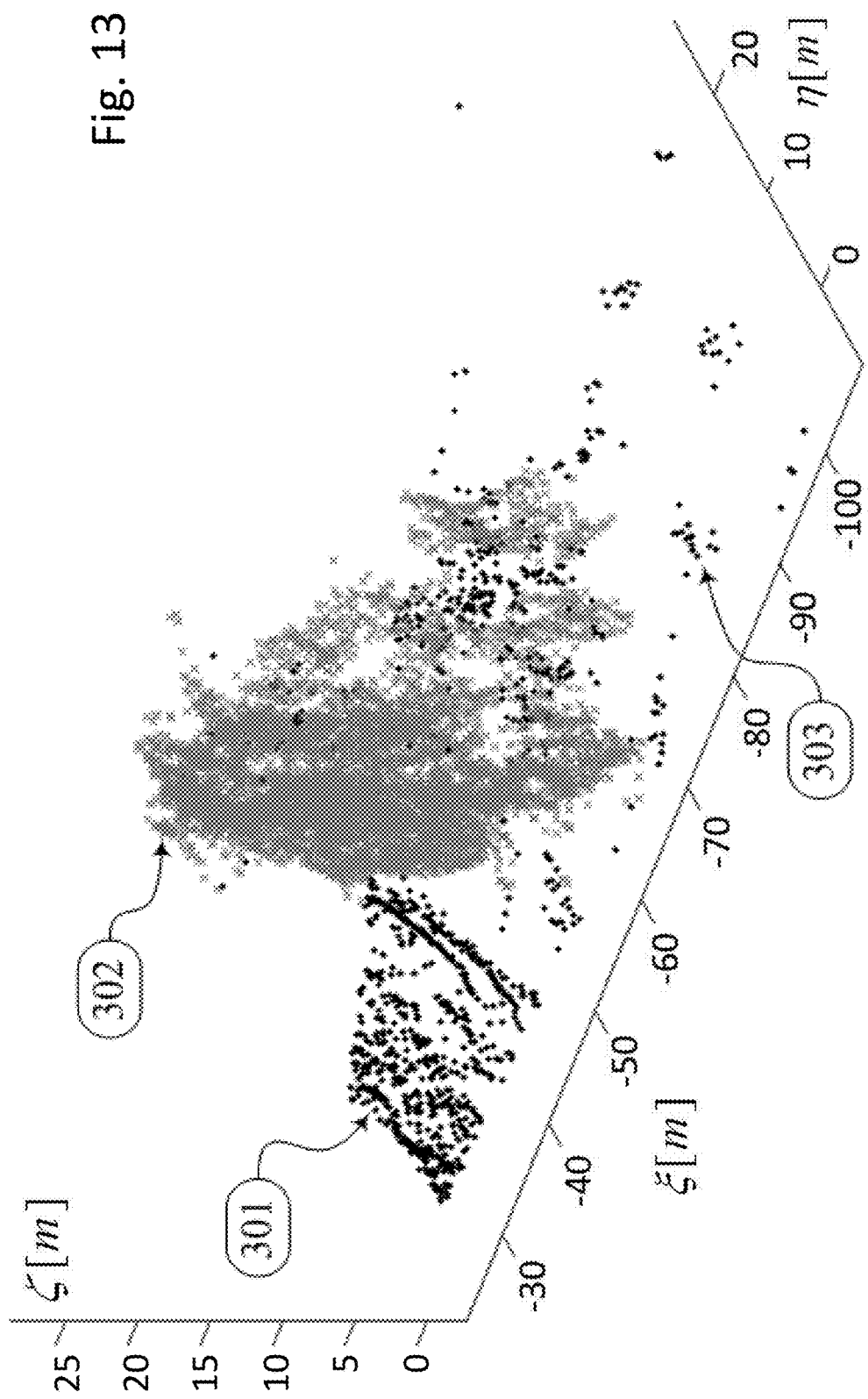
Figure 14:
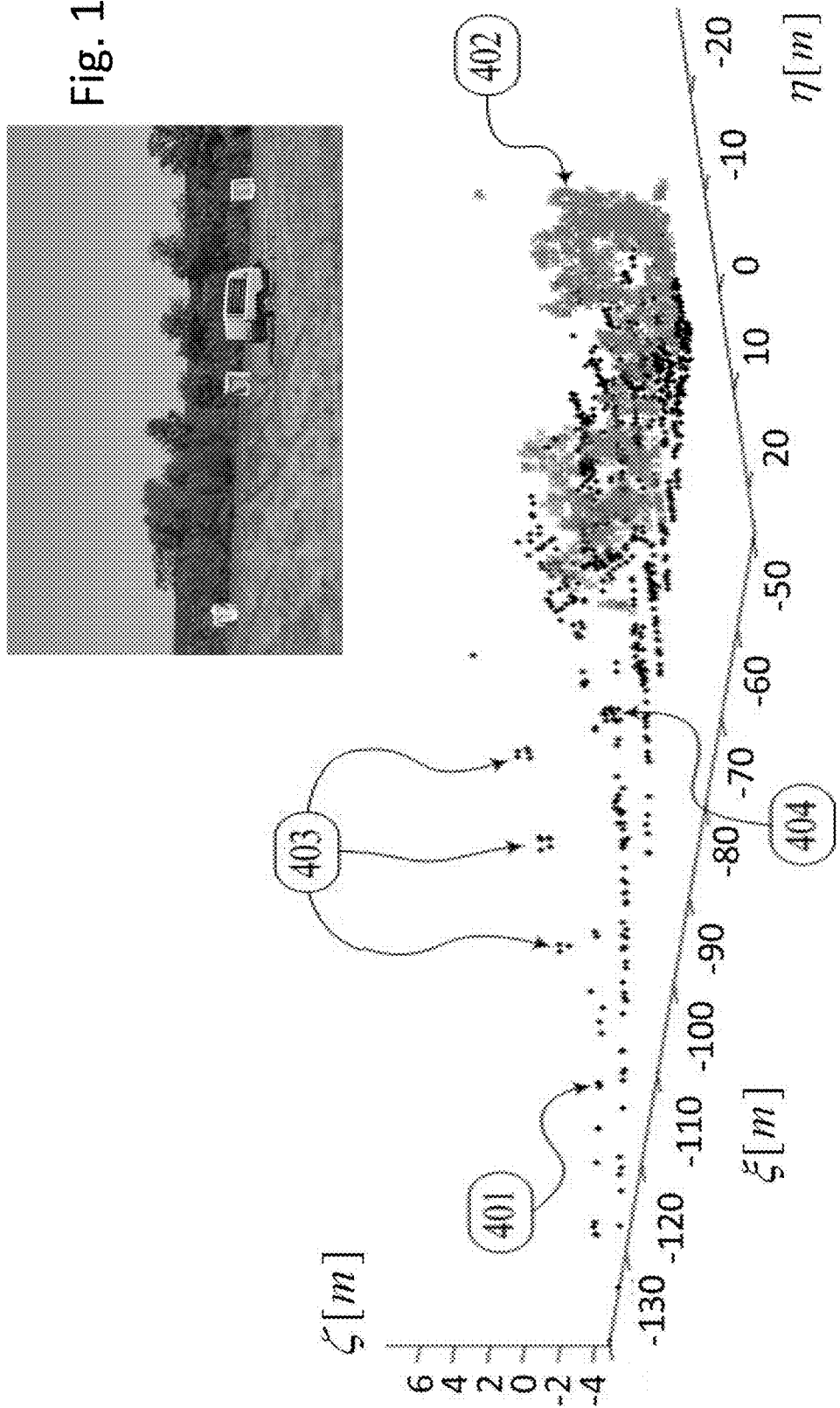
Figure 15:
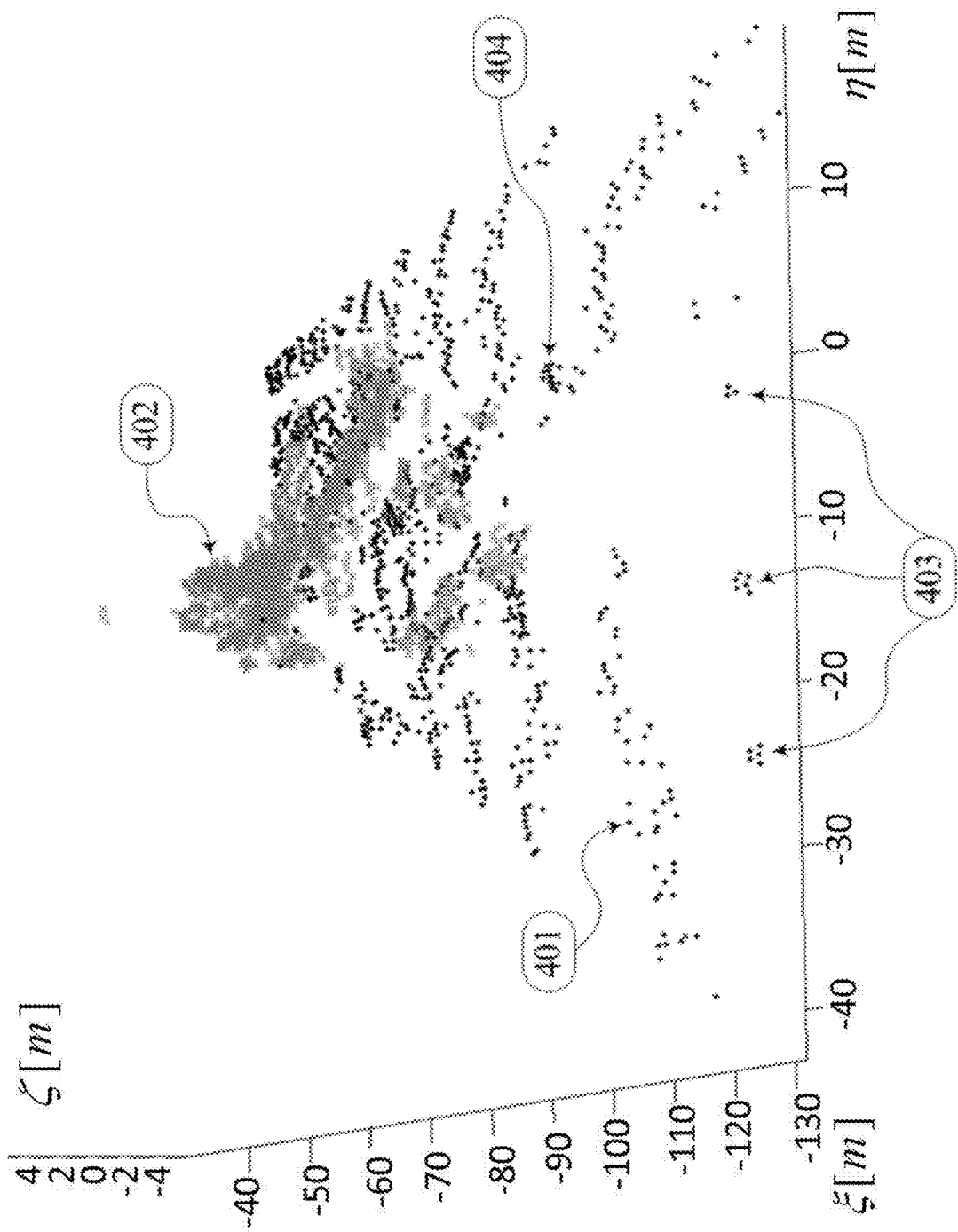

In the figures:

FIG. 1 shows the minimal scan region of a laser sensor for use of the method according to the invention, FIG. 2 shows the inhomogeneous particle density within a brownout dust cloud, FIG. 3 shows the intensity of the back reflected light of an individual laser pulse from a brownout dust cloud as a function of the penetration depth, FIG. 4 shows the probability distribution of a measurement value from a brownout dust cloud, FIG. 5 shows the imaging behavior of a multi-pulse laser sensor for a brownout landing, FIG. 6 shows the behavior versus time of the center of geometry of a brownout dust cloud and of a static obstacle lying behind the dust cloud in a top view, FIG. 7 shows the probability $P_{l,i}$ as a function of the variability of a cluster parameter in relation to the mean square deviation thereof from the respective average value, FIG. 8 shows an exemplary calculation result for a 3D arrangement of multiple dust clusters with the main direction axes and respective centroids thereof when using the method according to the invention, FIG. 9 shows a snapshot recording of the typical variation with time of the centroids and main direction axes orientation of volatile dust clusters in 3D space, FIG. 10 shows the behavior versus time of the centroids and main direction axes of real static obstacles, FIG. 11 shows the projected set T(ΣPi) of a segmented dust cloud from a real brownout test when using the method according to the invention, FIG. 12 shows a perspective 3D view of the segmented brownout dust cloud of FIG. 11 when using the method according to the invention, FIG. 13 shows a further 3D view of the segmented brownout dust cloud of FIG. 11 when using the method according to the invention, FIG. 14 shows a segmented brownout cloud in a perspective 3D view and the photo of the associated scene with real obstacles behind the brownout cloud when using the method according to the invention, FIG. 15 shows the rear 3D view of the scene from FIG. 14.

DETAILED DESCRIPTION

The exemplary embodiment described below is specifically focused on a helicopter landing while a brownout is occurring. Accordingly, the following description applies to all mentioned aerosol clouds as well as application cases (mobile, static use).

The present invention involves a method that, based on high resolution 3D laser data, is capable of detecting the turbulent dust, segments and removes the dust from the pilot's synthetic display (for example helmet visor, HUD or monitor). This method allows the user, in particular for a pilot, to practically look through the dust and thus avoid a loss of spatial orientation in the event of a brownout. Even the detection of relatively small obstacles, for example in the landing zone of a helicopter, through the brownout cloud is achievable.

In order to be able to detect turbulent sand and dust for the purposes of the invention algorithmically, the laser sensor used should preferably scan a sufficiently large horizontal and vertical field of view (FOV) in front of the helicopter in the direction of the current flight path thereof. The required 3D data of the sensor are advantageously available in real time. The data can be obtained, for example, with a SferiSense® laser sensor that is typically mounted on the helicopter.

For this purpose, it is particularly advantageous if the 3D data per recording cycle (a so-called frame) of the laser sensor comprise multiple measurement data echoes per laser pulse (so-called multi-pulse data).

The maximal detection range of the laser sensor used should preferably be at least 50 m and the distance in front of the helicopter for the detection of the nearest measurement point should preferably not be greater than 25 m, i.e. may not be further away than 25 m in front of the helicopter, in order to enable calculations for the purposes of the present invention to be carried out in an optimal manner. Thus, in a preferred implementation the following minimum requirements arise in relation to the "forward-looking" field of view (FOV) of the laser sensor used:

minimum horizontal field of view: $\phi_{min} := \pm 15°$
minimum vertical field of view $\theta_{min} := \pm 15°$
minimum distance measurement interval $R_{min} := [25\ m, 50\ m]$ FIG. 1 shows the minimum horizontal scan region of a laser sensor that can be used for the method. The reference characters indicate the sensor position 101 above the landing area $\xi\eta \subset R^2$, the field of view of $\pm 15°$, as well as the hatched minimum detection region "horizontal FOV" 106 of the laser sensor that lies within the minimum distance measurement interval of [25 m, 50 m]. The FOV extends in the direction of flight for use in a helicopter, or in the direction of travel or in the direction of view for other application areas.

The method according to the invention advantageously makes use of the superficial weakness of laser sensors during brownout situations by analyzing the natural densification of the sensor measurement values at the front side of a brownout dust-cloud. As a result, an apparent disadvantage of the physical detection properties of a laser sensor, namely its inability to "look-through" the dust-cloud, is converted into an algorithmic advantage that enables brownout dust turbulences in front of the helicopter to be detected and hence segmented from real obstacles and the ground behind the same. The segmentation of the dust in turn enables multi-pulse laser sensors to be used to look-through the dense brownout cloud—similarly to radar systems, but without the main disadvantages thereof—in particular in respect of their significantly poorer spatial resolution.

For this purpose, initially—with advantageous use of the physical detection properties of a brownout cloud by laser sensors—certain subsets that already contain indications of the potential association with the brownout cloud are determined based on the 3D information of just a single sensor frame.

For the mathematical calculation method presented below, characteristic properties of the 3D measurement data during a brownout landing are determined. For this purpose, the raw measurement data of the laser sensor, typically consisting of azimuth $\phi$, elevation $\theta$ and measurement distance r, are transformed by means of a suitable transformation $f_P$ into a point cloud within the Euclidean space $R^3$:

$$f_P : R^3 \to R^3(\phi, \theta, r) \mapsto f_P(\phi, \theta, r) := (\xi, \eta, \zeta)^t \qquad (1)$$

The resulting point cloud P can thus be denoted as:

$$P := \{(\xi, \eta, \zeta)^t \in R^3\} \qquad (2)$$

Let m be the number of laser pulses per sensor frame and n the number of measurement values per laser pulse, then $\Sigma P_i$ denotes the combination of the point clouds $P_k$ of all measurement values of the $i^{th}$ frame of the laser sensor over all pulses:

$$\sum P_i := \bigcup_m \left( \bigcup P_k \right) k \in \{1, \ldots, n\}, i, m \in N \qquad (3)$$

Considering an individual measurement value of the point cloud $\Sigma P_i$ as the manifestation of the random variable X with a probability of occurrence p(r) that is dependent on the distance, then the physical laser measurement of an extended, non-solid spatial object, such as represented by a brownout cloud, corresponds to a Bernoulli process or a dichotomous search scheme. The accumulation of the measurement values in $\Sigma P_i$ is thus based on a binomial distribution.

For an isolated brownout cloud the following qualitative characteristic properties arise due to the physical detection properties of laser sensors as well as the distribution of the turbulent particles within the dust cloud:

The particle density $\rho(r)$ within the dust cloud is not homogeneous over the entire spatial depth of the cloud, but varies with the distance r (this is illustrated in FIG. 2):

The further a laser beam penetrates into the dust cloud, the greater is the already scattered component of the light energy thereof. It follows from this that the intensity I(r) of the light reflected back from within the dust cloud decreases markedly with increasing penetration depth r, more accurately stated, is folded with a Lambert-Beer absorption profile (this is illustrated in FIG. 3):

Due to the decrease in intensity with increasing penetration depth, the detection probability p(r) for an individual measurement value of the point cloud $\Sigma P_i$ also decreases markedly with increasing penetration depth into the brownout cloud (this is illustrated in FIG. 4):

The following physical imaging behavior of laser sensors arises from the qualitative probability distribution of the dust-measurement values in FIG. 4:

There is an accumulation of measurement values of the point cloud $\Sigma P_i$ at the front of the brownout cloud facing the helicopter—there is a natural intensification of measurement values here. In contrast thereto, the rear side of the brownout cloud facing away from the helicopter is practically not detected by a laser sensor due to the decrease in intensity of the back-reflected light (cf. FIG. 3). The measurement of the point cloud $\Sigma P_i$ therefore spatially presents a kind of hollow figure of the dust cloud, of which only the front side exists.

In FIG. 5 this behavior is illustrated in principle in the $\xi, \zeta$ plane. It shows the physical imaging behavior of a multi-pulse laser sensor during a brownout-landing.

Based on the sensor position 101 in the direction of flight, there is an densification of measurement values at the front side of the dust cloud 103. On the other hand practical measurement tests during brownout landings with laser sensors, such as for example SferiSense® sensors, show that in particular the last measurement value 104 of a laser pulse frequently fully penetrates the brownout cloud 102, and thus real obstacles 105 or the ground behind the dust cloud can be detected.

The method according to the invention makes advantageous use of the general physical detection properties of laser sensors described in the preceding section—in particular the typical densification of the measurement values of $\Sigma P_i$ on the side of a brownout cloud facing the sensor. The ostensible disadvantage of laser sensors with respect to the described densification of measurement values due to physical detection properties is used below by the method according to the invention as a detection advantage in the mathematical algorithm sense by determining related dense subsets of $\Sigma P_i$ (so-called clusters). The cluster relationship is given in a natural way by the local point density in $\Sigma P_i$. Due to the physically based vertical structure and the natural distribution of the measurement values of $\Sigma P_i$, the local point density increases once again at the front side of the brownout cloud if $\Sigma P_i$ is projected into a plane $\xi\eta$ that is parallel to the landing surface:

$$T: R^3 \to R^2 (\xi,\eta,\zeta)^t \mapsto T(\xi,\eta,\zeta) := (\xi,\eta)^t, \text{ with} \quad (\xi,\eta,\zeta)^t \in \Sigma P_i \quad (4)$$

The set of projected measurement values from $\Sigma P_i$ is defined as:

$$T(\Sigma P_i) := U \subset R^2 \quad (5)$$

A local point density in U can for example easily be determined using the Chebyshev metric (wherein other metrics, such as for example the Euclidean metric, can be used)

$$\forall a,b \in U: d(a,b) := \max\{|\xi_a - \xi_b|, |\eta_a - \eta_b|\} \quad (6)$$

For this a, b are points from the set U and d(a,b) defines the distance between the points a and b.

The basic idea of the cluster formation based on the local point density in U is related to a well-defined, minimum neighborhood $B_{d_{min}}$ with:

$$B_{d_{min}}(a) := \{b \in U | d(a,b) \leq d_{min}\}, a \in U, d_{min} = \text{const.} \quad (7)$$

(wherein $B_{d_{min}}(a)$ denotes a neighborhood around the point a in which the distance to a given adjacent point b lies below the determined threshold value $d_{min}$), a minimum number $n_{min}$ of adjacent points must be contained. Therefore, the point density in $B_{d_{min}}$ must be greater than a specified lower limit:

$$|B_{d_{min}}(a \in U)| \geq n_{min}, n_{min} = \text{const.} \quad (8)$$

As can easily be shown, the criterion (8) for a cluster formation in U is necessary but not sufficient, because one must distinguish, inter alia, between core points in the interior of a cluster and points near or at the border of the cluster during the formation of connected components. It is immediately apparent that as a rule the local point density in the neighborhood $B_{d_{min}}$ of an border point is typically smaller than the corresponding point density of a core point. The recursive definition of a density-dependent cluster C over U given below takes into account the inequality of the local point density between core and border points in the usual way and at the same time forms the basis for the type of formation of connected components that is used here:

$$\text{Def.: density-dependent cluster} \quad (9)$$

$C \subseteq U$ is a density-dependent cluster $\overset{def}{\Leftrightarrow}$ (1) $\forall a, b \in U: a \in C \wedge a \overset{P}{\longmapsto} b \Rightarrow b \in C$ (2) $\forall a, b \in C: a \overset{c}{\longleftrightarrow} b$ The intuitive notation of definition (9) borrowed from graph theory shall be understood as follows:

$$\text{Def.: connectedness of two} \quad (10)$$
$$\text{points of a density-dependent cluster } C \subseteq U$$

$a \in C$ is connected to $b \in C$(in characters $a \overset{c}{\longleftrightarrow} b$) $\overset{def}{\Leftrightarrow}$ $\exists c \in C: c \overset{P}{\longmapsto} a \wedge c \overset{P}{\longmapsto} b$ Definition (10) describes the connectedness between two cluster points a,b∈C concerning the existence of a third adjacent cluster point c∈C.

$$\text{Def.: indirect adjacency of two points in } C \subseteq U \quad (11)$$

$a \in C$ is indirectly adjacent to $b \in C$(in characters $b \overset{P}{\longmapsto} a$) $\overset{def}{\Leftrightarrow}$ $\exists p_1, \ldots, p_n \in C$ with $p_1 = b \wedge p_n = a: p_i \longmapsto p_{i+1}$, $i \in \{1, \ldots, n\}$, $n \in N$ Definition (11) describes two cluster points a,b∈C as indirectly adjacent if they are connected by a path consisting of a finite number of direct neighbors.

$$\text{Def.: direct adjacency of two points in } C \subseteq U \quad (12)$$

$a \in C$ is directly adjacent to $b \in C$(in characters $b \longmapsto a$) $\overset{def}{\Leftrightarrow}$ (1) $a \in B_{d_{min}}(b)$ (2) $|B_{d_{min}}(b)| \geq n_{min}$ Definition (12) describes a∈C as directly adjacent to b∈C if a∈C lies within the neighborhood $B_{d_{min}}$ of b∈C and the neighborhood consists of at least $n_{min}$ points—including a,b∈C (cf. (8)).

Due to the transformation T of (4), the clusters formed using the definition (9) can contain some measurement points from the ground. Therefore, it is necessary to carry out a ground segmentation local to the cluster.

Taking into account the directly available, fully 3D information of a measurement point from $\Sigma P_i$, for this purpose let:

$$p_i = (\xi_i, \eta_i, \zeta_i)^t \in C \quad (10)$$

Be a point of the cluster C over U that lies within the neighborhood $B_{d_{min}}$ of (7). If now:

$$\Delta \zeta = |\zeta_i - \zeta_j| < \epsilon \quad \forall p_i, p_j \in B_{d_{min}}, i \neq j \quad (11)$$

with a suitable $\epsilon > 0$, then the points from $B_{d_{min}}$ practically lie in a local plane, which normal vector deviates just slightly from the vertical direction. If in addition the points from $B_{d_{min}}$ lie on the lower base of the cluster C, then the same are ground points that are local to C. The local ground points are removed from further calculations, because they would distort the detection of dust clusters.

Due to the physical imaging properties of laser sensors, it is possible to identify all brownout dust measurement data from a single sensor frame without the need for further measurement data accumulation using the cluster formation based on the local point density over the projection set U. According to the same logic, all point clusters that relate to real obstacles in the landing zone are also obtained.

By way of the described cluster-local ground segmentation, the result of the single-frame calculation consists of two disjoint sets of points:

1) Set of all m point density-based clusters of the $i^{th}$ sensor frame:

$$\Sigma C_i := \cup C_k, k \in \{1, \ldots, m\}, i \in \{1, \ldots, n\}, n, m \in N \quad (12)$$

2) Rest of remaining sensor measurement data:

$$R_i := \Sigma P_i \setminus \Sigma C_i \quad (13)$$

Due to the design of the method, the set $R_i$ consists practically of only the ground measurement values of the landing area. The set $\Sigma C_i$ on the other hand comprises both all dust clusters and also all clusters belonging to real obstacles In a further step of the method, each cluster $C_k \subseteq \Sigma C_i$, $k \in \{1, \ldots, m\}$ is projected onto a plane that is orthogonal to the landing surface and that is additionally rotated about the angle $\psi$ of the horizontal center of view of the sensor FOV and is therefore orthogonally to the direction of view of the sensor. Here again, the full 3D information of a point of the cluster $C_k$ will be used, resulting in the following transformation:

$$S_\psi : R^3 \to R^2 (\xi, \eta, \zeta)^t \mapsto S_\psi(\xi, \eta, \zeta) := (u, v)^t \text{ with } (\xi, \eta, \zeta)^t \in C_k \quad (14)$$

Hence the set of projected cluster points can be defined as:

$$S_\psi(C_k) := V \subset R^2 \quad (15)$$

Using the transformation (17), an upright projection of each individual cluster $C_k$ is obtained. Local sub components of the cluster $C_k$ can be determined on the projection set V, which in turn can be treated as independent clusters or can be recursively divided into further sub-sub components including the full 3D information. The result is an expanded set of $\hat{m}_i \in N$ disjoint, uniquely identifiable point clusters $\hat{C}_l$ of the $i^{th}$ sensor frame:

$$\Sigma \hat{C}_i := \cup \hat{C}_l, l \in \{1, \ldots, \hat{m}_i\}, i \in \{1, \ldots, n\}, \hat{m}_i, n \in N \quad (16)$$

The value of $\hat{m}_i$ depends both on the spatial resolution of the laser sensor in use and the measurement distance and also on a parameterisable "Level of Detail" that is desired to be achieved during the cluster formation. An individual fine tuning of these parameters is usefully carried out by means of a heuristic based on real measurement data of brownout landings.

Following the cluster formation, unique characteristic features are calculated for each cluster $\hat{C}_l \subseteq \Sigma \hat{C}_i$, $l \in \{1, \ldots, \hat{m}_i\}$. Among others, the following cluster features are of particular significance for this:

a) Geometric center of cluster as a position feature:
Let $n = |\hat{C}_l|$ be the number the points of the cluster $\hat{C}_l \subseteq \Sigma \hat{C}_i$, then the associated cluster center point is defined as the vector:

$$s := \left( \frac{1}{n} \sum_i \xi_i, \frac{1}{n} \sum_i \eta_i, \frac{1}{n} \sum_i \zeta_i \right)^t \in R^3, i \in \{1, \ldots, n\} \quad (17)$$

b) spatial orientation of the major axis of the cluster as a orientation feature:
If $\lambda_1, \lambda_2, \lambda_3 \in R$ denote the real-value Eigen values of the inertial tensor $T(\hat{C}_l)$ for the cluster $\hat{C}_l \subseteq \Sigma \hat{C}_i$, then the direction of the major axis $v \in R^3$ of the cluster can be uniquely determined as the Eigen vector for the smallest magnitude Eigen value $\lambda_{min}$ by means of:

$$(T(\hat{C}_l) - \lambda_{min} I) v = 0 \quad (18)$$

with the unit matrix I.

c) Cluster eccentricity as a shape feature:
The eccentricity $\epsilon$ of a cluster $\hat{C}_l$ is easily calculated by means of the centered second moments $\mu_{2,0}, \mu_{1,1}, \mu_{0,2}$ $$\varepsilon(\hat{C}_l) = \frac{(\mu_{2,0}(\hat{C}_l) - \mu_{0,2}(\hat{C}_l))^2 + 4\mu_{1,1}^2(\hat{C}_l)}{(\mu_{2,0}(\hat{C}_l) + \mu_{0,2}(\hat{C}_l))^2} \quad (19)$$

Here the calculation of the eccentricity is advantageously carried out both by means of $T(\hat{C}_l)$ (cf. (4)) and also by means of $S_\psi(\hat{C}_l)$ (cf. (17)). As a result, two separate shape features $\epsilon_{\xi\eta}$ and $\epsilon_{uv}$ are obtained for unique characterization of one and the same cluster $\hat{C}_l \subseteq \Sigma \hat{C}_i$.

Up to this point the calculation according to the invention has been carried out on a single sensor frame. Using the disjoint remaining set $R_i$ (cf. (16)), all ground points have been separated from the revealed clusters. The 3D clusters were in turn determined by operations in the $R^2$ and sufficiently refined depending on sensor resolution and measurement distance according to a parameterizable "Level of Detail". Then unique characteristic features for position, spatial orientation and shape were derived for each cluster.

During the further modus operandi, information is now obtained from a sequence of a multiple sensor frames. Due to the calculation results from the single-frame processing, it is advantageously possible here—in contrast to the state of the art—to continue calculations with only the frame-based, characteristic cluster features described above.

The set $\Sigma \hat{C}_i \subseteq \Sigma \hat{P}_i \subset R^3$ contains both all dust measurement values and also all of those measurement values that relate to real obstacles. It will be shown below how the dust measurement values can be simply and elegantly distinguished from the obstacle measurement values:

It is a significant property of brownout clouds or subsets thereof that they continuously change position above the ground versus time t due to the helicopter's own movements and the air flow of its main rotor. A brownout cloud is per se a volatile, non-fixed object. For this reason, the geometrical center of the cloud, in contrast to real obstacles, has no fixed position over the time t, as illustrated in FIG. 6 in a top view ($\xi\eta$ plane).

The front 201 of the brownout cloud detected by the laser sensor changes continuously versus time t. The change in the position of the centroid 202 of the same brownout cloud is detected at times $t_0$, $t_1$, $t_2$, but by contrast the real obstacle 105 and the associated centroid 203 thereof remain fixed in position. The variation with time of the position of the centroid of the brownout cloud or subsets thereof correlates with an analogous variation with time of the associated orientation of the major axis and the eccentricity.

For real obstacles, the following relationships exist naturally, wherein l denotes the cluster and i denotes the frame:

Let $$s^{(l,i)}: R^+ \to R^3, t \mapsto s^{(l,i)}(t) := (\xi_s^{(l,i)}(t), \eta_s^{(l,i)}(t), \zeta_s^{(l,i)}(t))^t \quad (20)$$

be the position vector function of the centroid s for a cluster $\hat{C}_l \subseteq \Sigma \hat{C}_i$, $l \in \{1, \ldots, \hat{m}_i\}$, $i \in \{1, \ldots, n\}$ as a function of t, then for a real obstacle cluster the following applies $$s^{(l,i)}(t) \cong \text{const.} \quad \forall t \in R^+ \quad (21)$$

Let $$v^{(l,i)}: R^+ \to R^3, t \mapsto v^{(l,i)}(t) := (\xi_v^{(l,i)}(t), \eta_v^{(l,i)}(t), \zeta_v^{(l,i)}(t))^t \quad (22)$$

be the direction vector function of the major axis v for a cluster $\hat{C}_l \subseteq \Sigma \hat{C}_i$, $l \in \{1, \ldots, \hat{m}_i\}$, $i \in \{1, \ldots, n\}$ as a function of t, then for a real obstacle cluster the following applies:

$$v^{(l,i)}(t) \cong \text{const.} \quad \forall t \in R^+ \quad (23)$$

Let $$\epsilon_{\xi\eta}^{(l,i)}: R^+ \to [0,1], t \mapsto \epsilon_{\xi\eta}^{(l,i)}(t) := a^{(l,i)}$$

$$\epsilon_{uv}^{(l,i)}: R^+ \to [0,1], t \mapsto \epsilon_{uv}^{(l,i)}(t) := b^{(l,i)} \quad (24)$$

be the cluster-eccentricity relating to the transformations T and $S_\psi$ (cf. (4), (17)) for a cluster $\hat{C}_l \subseteq \Sigma \hat{C}_i$, $l \in \{1, \ldots, \hat{m}_i\}$, $i \in \{1, \ldots, n\}$ as a function of t, then the following applies for a real obstacle cluster:

$$\epsilon_{\xi\eta}^{(l,i)}(t) \cong \text{const.} \quad \forall t \in R^+$$

$$\epsilon_{uv}^{(l,i)}(t) \cong \text{const.} \quad \forall t \in R^+ \quad (25)$$

Using equations (23), (25) and (27), the variations with time of the centroid, major axis and eccentricity of a cluster can be advantageously described.

For further analysis, for each of the parameters for a cluster $\hat{C}_l \subseteq \Sigma \hat{C}_i$, advantageously a probability $P_{l,i}$ is introduced depending on the variability in relation to the mean square deviation thereof from the respective average value over $n \in N$ sensor frames—wherein outliers for which the empirical standard deviation of a parameter is greater than the associated average value are excluded from further consideration.

For this, let D be a suitable definition range and $$P_{l,i}: D \to [0,1], A^{(l,i)} \mapsto P_{l,i}(A^{(l,i)}) := \left(1 - \frac{\left|\sqrt{n \sum_i (A^{(l,i)})^2 - \left(\sum_i A^{(l,i)}\right)^2}\right|}{\left|\sum_i A^{(l,i)}\right|}\right)^2 \quad (26)$$

for $i \in \{1, \ldots, n\}$ and $l \in \{1, \ldots, \hat{m}_i\}$, with the substitution of the random event $A^{(l,i)}$:

$$A^{(l,i)} = s^{(l,i)} \lor A^{(l,i)} = v^{(l,i)} \lor A^{(l,i)} = \epsilon_{\xi\eta}^{(l,i)} \lor A^{(l,i)} = \epsilon_{uv}^{(l,i)} \quad (27)$$

FIG. 7 shows the probability $P_{l,i}$ over D:

The probability $P_{l,i}$ is constructed such that with increasing variability of a parameter versus the respective average value thereof, the probability of a static state decreases by a square law.

By means of the substitution (30), four individual probabilities for the variables (23), (25) and (27) for each cluster $\hat{C}_l \subseteq \Sigma \hat{C}_i$, $l \in \{1, \ldots, \hat{m}_i\}$, $i \in \{1, \ldots, n\}$ are defined over n sensor frames. For the characterization of a cluster, the individual probabilities are combined to form a weighted total probability.

Let $\kappa_1, \ldots, \kappa_4 \in R$ be suitable weights for this, then the total probability $\hat{P}_{l,i}$ that a cluster $\hat{C}_l \subseteq \Sigma \hat{C}_i$ is a static real obstacle is defined by:

$$\hat{P}_{l,i}(\hat{C}_l \subseteq \Sigma \hat{C}_i) := \kappa_1 P_{l,i}(s^{(l,i)}) + \kappa_2 P_{l,i}(v^{(l,i)}) + \kappa_3 P_{l,i}(\epsilon_{\xi\eta}^{(l,i)}) + \kappa_4 P_{l,i}(\epsilon_{uv}^{(l,i)}) \in [0,1] \quad (28)$$

Using the total probability $\hat{P}_{l,i}$, it can now easily be validated whether a cluster represents a static real obstacle within useful reliability limits. Because of the construction of $\hat{P}_{l,i}$ and the resulting analysis of the characteristic parameter over n-sensor frames, it is advantageously possible to calculate a corresponding result for the current sensor frame without the need to consider the totality of all measurement points of the last n sensor frames again. This is a very computation efficient behavior of the method according to the invention compared to known calculation methods.

Due to the freely parameterisable "Level of Detail" during the cluster formation, components of brownout clouds and real obstacles can always be decomposed into pairs of disjoint subsets of $\Sigma P_i$. Therefore, the dust clusters at the end of the presented computation can easily be identified by the negation:

$$\neg \hat{P}_{l,i}(\hat{C}_l \subseteq \Sigma \hat{C}_i), l \in \{1, \ldots, \hat{m}_i\}, i \in \{1, \ldots, n\} \quad (29)$$

Moreover, to refine the described cluster validation, further specific parameters, such as, for example: number of measurement values per cluster, relative adjacency, cluster of clusters or subdivision into shape-dependent sub-components (so-called form primitives) can be advantageously incorporated into the calculation.

The particular approach of the presented method during the processing of the 3D data for segmenting a brownout cloud regarding the probability $\hat{P}_{l,i}$ lies in the characterization of the variation versus time of density-dependent measurement point clusters over n sensor frames using abstract discrete parameters for position, spatial orientation and shape—and hence not by means of a computationally-intensive accumulation of a very large number of isolated individual measurement points over multiple sensor frames and their global mathematical analysis thereof, as is usual according to the current state of the art.

The functionality of the data processing according to the invention, in particular the formation of clusters from brownout dust clouds based on real measurement data of brownout tests, is demonstrated by way of example using a series of graphs.

Here by way of example it is made significant how measurement point clusters are formed from a single sensor frame using the natural measurement point density and the local measurement point distribution within the brownout cloud due to the physical imaging properties of laser sensors. By the calculation of characteristic properties for position, spatial orientation and shape of the measurement point cluster as well as the analysis and validation of the variation with time of the parameters over multiple sensor frames, it is possible to segment the brownout cloud reliably from the set of measurement data and hence finally to filter out the brownout cloud. The following graphs demonstrate how as a result the orientation of the pilot and his situational awareness can be increased as well as the detection of real obstacles in brownout situations can be significantly improved.

An exemplary calculation result of the clustering of a brownout cloud according to the invention is illustrated in FIG. 8. A perspective, 3-dimensional arrangement of multiple dust clusters 501 can be seen (the example shows 8 clusters, which are composed of real measurement points of a laser sensor) with the different orientations of the main axes 502 thereof and the respective centroids 503.

As the dust clusters are naturally time variant, their corresponding characteristic features vary with time. FIG. 9 shows by way of example a snapshot recording of the typical time response of the centroid 601 and the main axes orientation 603 of volatile dust clusters in 3-dimensional space (here in the orthographic projection in the $\xi\eta$ plane) based on real calculation results from multiple sensor frames.

Here 602 denotes a cluster, the centroid of which remains practically positionally fixed versus time over two sensor frames, but the main axes orientations of which differ significantly from each other. 604 shows the variation of the position of the centroid and the main axes orientation of a further dust cluster at the discrete times $t_0, \ldots, t_3$.

The data that are important and relevant for the user form real, positionally fixed obstacles. In FIG. 10, two calculation examples of the behavior versus time of real static obstacles are seen. The centroids 701, 702 and 703 remain practically positionally fixed over time. The main axes orientation (dashed lines) of the obstacle cluster is nearly the same within narrow numerical limits or point in the direction opposite thereto, which in turn is equivalent in respect of the basic orientation of the obstacle. Occasional outliers of the main axes orientation are not significant and can be neglected during the consideration of multiple sensor frames.

Consideration is now given by way of example in FIG. 11 to the projected set $T(\Sigma P_i)$ from (5) with the segmented dust cloud from a real brownout test over the $\xi\eta$ plane. Following the conclusion of the dust segmentation according to the invention, ground measurement points 301 in front of the dust cloud, the measurement points of the segmented brownout cloud 302 itself and in turn ground measurement points 303, in this case behind the cloud, are detected.

The point set of the same scene of FIG. 11 is shown in FIG. 12 in a perspective 3D view. The ground measurement points 301 in front of the dust cloud, the measurement points of the segmented brownout cloud 302, and the ground measurement points 303 behind the cloud can again be seen here. FIG. 13 shows a similar illustration of the same scene from a different angle of view, wherein each illustration is carried out from a position that does not correspond to the original laser sensor position.

In order to illustrate that the segmented measurement data correlates with reality, a real environment with obstacles in the landing zone is illustrated in FIG. 14 by way of example. In this case a photographic image of the landing zone before the brownout is shown (small photo in the upper edge of the image), as well as the associated dust cloud segmented according to the invention (as a result of the described data processing) in the brownout during the helicopter landing, which is shown in a perspective 3D view.

The ground measurement points 401, the segmented dust cloud 402, as well as an arrangement of three obstacles 403 in the background and an isolated obstacle 404 at a shorter distance can be seen here. Using FIG. 14, the advantage of the present invention is shown; a clear and unambiguous discriminability between the dust cloud, the ground and obstacles is achieved.

FIG. 15 shows the rear 3D view of the scene from FIG. 14 with obstacles 403 and 404 behind the brownout cloud 402 above the ground measurement points 401.

From this it can be seen that the method according to the invention enables a reliable and very efficient segmentation of the dust cloud, and hence practically enables a view through the turbulent dust, which avoids a loss of spatial orientation of the pilot in the event of a brownout.

Even the detection of relatively small obstacles in the landing zone of a helicopter through the brownout cloud is possible, as FIG. 14 and FIG. 15 show by way of example using real 3D measurement data, with the segmentation method according to the invention.

Furthermore, the method according to the invention allows an avionic system with real-time capability suitable for operational use for pilot support of helicopter landings specifically under brownout conditions. The present invention is not necessarily limited to aircraft, because the use of the described dust segmentation could also be advantageous in other mobile vehicles or even at stationary positions. The method according to the invention can in particular be advantageously implemented in a system comprising a laser sensor, a data processing unit as well as an output device.

The data processing unit segments and filters the physically measured 3D data using the calculation process according to the invention, such that on the output device (for example in a synthetic view of the environment, for example on a helmet visor, HUD or monitor) only the relevant information are displayed, i.e. ground and real obstacle data; therefore, the associated brownout dust data are filtered out. In the FIGS. 11 to 15 this means that the segmented dust clouds 302, 402 are removed from the display data of the output device, which in particular is of great importance for the spatial orientation and the situational awareness of the pilot as well as for the assessment of the obstacle situation, because without the described method the brownout cloud is located in the direct field of view of the pilot.

Although the present invention has been described above by means of embodiments with reference to the enclosed drawings, it is understood that various changes and developments can be implemented without leaving the scope of the present invention, as it is defined in the enclosed claims.

The invention claimed is:

1. A method for detecting a location of an obstacle based on 3D sensor data of a 3D laser sensor, the method comprising:
    receiving the 3D sensor data;
    transforming the 3D sensor data into a 3D measurement point cloud;
    determining, based on local measurement point density, measurement point clusters from the 3D measurement point cloud of a single measurement cycle of 3D sensor related subsets;
    determining at least one of the following characteristic parameters of individual measurement point clusters
        position,
        orientation in space,
        shape,
    determining time variation of the characteristic parameters using 3D sensor data recorded in subsequent measurement cycles; and
    producing an association of a measurement point cluster to a real obstacle or an association of a measurement point cluster to the aerosol cloud based on the determined time variation of the characteristic parameters.

2. The method of claim 1, wherein the determination of the measurement point clusters is performed based on a projection of the 3D measurement point cloud in a horizontal plane.

3. The method of claim 2, further comprising:
clustering based on a projection of a previously determined measurement point cluster in a vertical plane that is oriented orthogonally to the horizontal main direction of view of the 3D sensor.

4. The method of claim 1, wherein 3D measurement points representing local ground surface are eliminated from the determined measurement point clusters.

5. The method of claim 1, wherein for each of the characteristic parameters of a determined measurement point cluster, an individual probability is determined depending on respective variability over multiple measurement cycles, and a total probability with which the measurement point cluster can be uniquely characterized as a real obstacle or an aerosol cloud is determined from the individual probabilities of the individual characteristic parameters of a measurement point cluster.

6. The method of claim 1, wherein the 3D sensor data are produced under brownout or whiteout conditions during take-off or landing of an aircraft.

7. The method of claim 1, wherein the 3D measurement point cloud is generated using a multi-pulse laser sensor, which returns multiple measurement points per emitted laser beam.

8. The method of claim 1, wherein the method is performed in real time based on 3D sensor data obtained continually during take-off or landing of an aircraft.

9. The method of claim 1, further comprising:
filtering, based on the produced association, the 3D sensor data to remove 3D sensor data with the measurement point cloud associated to the aerosol cloud; and
outputting the filtered, segmented 3D sensor data on a display, wherein the displayed filtered, segmented 3D data displays the real obstacle.

10. A method for segmenting 3D sensor data generated in presence of aerosol clouds to increase situation awareness and location detection of obstacles, the method comprising:
generating a multi-pulse laser;
receiving returns of the multi-point laser to produce multiple measurement points per emitted laser beam as 3D sensor data;
transforming the 3D sensor data into a 3D measurement point cloud;
determining measurement point clusters from the 3D measurement point cloud of a single measurement cycle of 3D sensor related subsets based on local measurement point density;
determining at least one of the following characteristic parameters of individual measurement point clusters
position,
orientation in space,
shape,
segmenting the 3D sensor data by producing an association of a measurement point cluster to a real obstacle or an association of a measurement point cluster to the aerosol cloud, wherein the association is produced by determining time variation of the characteristic parameters using 3D sensor data recorded in subsequent measurement cycles.

11. The method of claim 10, wherein the determination of the measurement point clusters is performed based on a projection of the 3D measurement point cloud in a horizontal plane.

12. The method of claim 11, further comprising:
clustering based on a projection of a previously determined measurement point cluster in a vertical plane that is oriented orthogonally to the horizontal main direction of view of the 3D sensor.

13. The method of claim 10, wherein 3D measurement points representing local ground surface are eliminated from the determined measurement point clusters.

14. The method of claim 10, wherein for each of the characteristic parameters of a determined measurement point cluster, an individual probability is determined depending on respective variability over multiple measurement cycles, and a total probability with which the measurement point cluster can be uniquely characterized as a real obstacle or an aerosol cloud is determined from the individual probabilities of the individual characteristic parameters of a measurement point cluster.

15. The method of claim 10, wherein the 3D sensor data are produced under brownout or whiteout conditions during take-off or landing of an aircraft.

16. The method of claim 10, wherein the method is performed in real time based on 3D sensor data obtained continually during take-off or landing of an aircraft.

17. The method of claim 10, further comprising:
filtering the segmented 3D sensor data to remove the segmented 3D sensor data with the measurement point cloud associated to the aerosol cloud; and
outputting the filtered, segmented 3D sensor data on a display, wherein the displayed filtered, segmented 3D data displays the real obstacle.

18. A system, comprising:
a 3D laser sensor;
an output device; and
a data processing unit coupled to the 3D laser sensor and the output device, wherein the data processing unit is configured to detect a location of an obstacle based on 3D sensor data of a 3D laser sensor by
receiving the 3D sensor data;
transforming the 3D sensor data into a 3D measurement point cloud;
determining, based on local measurement point density, measurement point clusters from the 3D measurement point cloud of a single measurement cycle of 3D sensor related subsets;
determining at least one of the following characteristic parameters of individual measurement point clusters
position,
orientation in space,
shape,
determining time variation of the characteristic parameters using 3D sensor data recorded in subsequent measurement cycles; and
producing an association of a measurement point cluster to a real obstacle or an association of a measurement point cluster to the aerosol cloud based on the determined time variation of the characteristic parameters.

* * * * *